United States Patent [19]

Itoh et al.

[11] Patent Number: 4,912,116

[45] Date of Patent: Mar. 27, 1990

[54] PROPIOPHENONE DERIVATIVES FOR TREATMENT OF POLLAKIURIA (FREQUENCY URINATION)

[75] Inventors: Yasuo Itoh, Katsuyamashi; Hideo Kato, Fukuishi; Eiichi Koshinaka; Kouji Morikawa, both of Katsuyamashi; Toshie Yamauchi, Ohnoshi, all of Japan

[73] Assignee: Hokuriku Pharmaceutical Co., Ltd., Katsuyamashi, Japan

[21] Appl. No.: 136,912

[22] Filed: Dec. 22, 1987

[30] Foreign Application Priority Data

Dec. 26, 1986 [JP] Japan .................... 61-308747

[51] Int. Cl.$^4$ ............... A61K 31/445; A61K 31/40
[52] U.S. Cl. ......................... 514/317; 514/320; 514/408; 514/428; 514/906
[58] Field of Search .............. 514/428, 408, 906, 317

[56] References Cited

U.S. PATENT DOCUMENTS 4,638,009  1/1987  Itho et al. .................... 514/428

OTHER PUBLICATIONS

Pietra et al., Chem. Abst. 105(11):91189u, (1986).
*The Merck Index*, 10th Ed., (1983), pp. 520, 1363, Reference Nos. 3555 and 9351.
Krupp, Marcus A., *Medical Diagnosis and Treatment*, (1976), p. 521.
*Physicians' Desk Reference*, 38th, (1984), p. 1900, Urispas.

Primary Examiner—Douglas W. Robinson
Attorney, Agent, or Firm—Gordon W. Hueschen

[57] ABSTRACT

A method for the treatment of pollakiurea in a subject in need thereof, comprising the step of administering to said subject an effective antipollakiurea amount of a propiophenone of the formula (I)

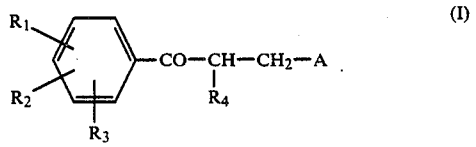

wherein $R_1$, $R_2$ and $R_3$ each independently represents hydrogen, halogen, lower alkyl- or halogeno-lower-alkyl, lower-alkoxy, or cycloalkyl having 3–8 carbon atoms, two of which $R_1$, $R_2$, and $R_3$ groups may combine to form methylenedioxy or ethyleneoxy, $R_4$ represents hydrogen or a lower-alkyl, and A represents pyrrolidinyl-, piperidinyl-, morpholinyl-, or azepinyl or a pharmaceutically-acceptable acid addition salt thereof, is disclosed.

7 Claims, No Drawings

PROPIOPHENONE DERIVATIVES FOR TREATMENT OF POLLAKIURIA (FREQUENCY URINATION)

FIELD OF THE INVENTION

This invention relates to a method for the treatment of frequency urination using a propiophenone derivative represented by general formula (I)

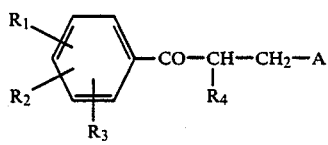

wherein $R_1$, $R_2$, and $R_3$, which may be the same or different, each independently represents hydrogen, halogen, lower alkyl- or halogeno- lower-alkyl group having a straight or branched carbon chain, a lower-alkoxy group, or a cycloalkyl group having 3–8 carbon atoms, two of which $R_1$, $R_2$, and $R_3$ groups may combine to form methylenedioxy or ethyleneoxy, $R_4$ represents hydrogen or a lower-alkyl group having a straight or branched carbon chain, and A represents pyrrolindinyl-, piperidinyl-, morpholinyl-, or azepinyl, or a pharmaceutically-acceptable acid addition salt thereof, as the therapeutically-active agent or principle.

DESCRIPTION OF THE PRIOR ART

The compounds represented by the general formula (I) are known and it is described for example in Jpn. Tokkyo Kokai (publication of unexamined patent application) 54-125630, 57-16841, 59-13771, 59-33276, 59-399869, 59-44371, 59-48474, 59-70665, 59-190980, 59-190981, 59-190982, 60-6675, 60-255767, 61-85379, 61-148172 and 61-207379 that some compounds thereof have muscular relaxation activity, spastic paralysis-activity, bactericidal effect, and antiallergic effect. See also U.S. Pat. No. 4,638,009, issued Jan. 20, 1987, describing some of these compounds for different uses than here claimed.

Especially, EPERISONE HCl (II) (generic name, the Merck Index, 10th Edition 3555, Jpn. Tokkyo Koho (publication) 55-27914) and TOLPERISONE HCl (III) (generic name, the Merck Index, 10th Edition 9351, Jpn. Tokkyo Koho 40-20390) are already on the market and have been widely provided for clinical usage in the treatment of muscular contractive and spastic paralysis.

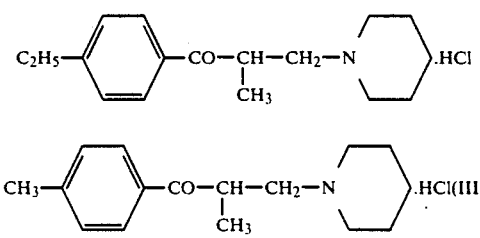

However, it was not known that compounds represented by the general formula (I) have utility in the treatment of diseases of the urinary tract, especially frequency urination.

PROBLEM TO BE RESOLVED

As a medicament for the treatment of pollakiuria (frequency urination) and residual urine resulting therefrom, accompanied by diseases of the urinary tract, such as inflammation of the bladder (cystitis) prostatitis and the like, it has been proposed to use a medicament which inhibits the urination reflex.

However, such medicaments are not only few, but their effects are moreover far from satisfactory. Therefore, the discovery and development of a novel and effective medicament, which eliminates impediments to micturition, has been long awaited by the medical profession.

SOLUTION OF THE PROBLEM

It has now been found that the propiophenone derivatives represented by the said general formula (I) and the pharmaceutically acceptable acid addition salts thereof are unexpectedly effective for inhibition of frequency urination-reflex in accordance with an obviously different kinetic mechanism compared with known central muscular relaxants, and the effect is superior to that of a known medicament for treatment of frequency urination, FLAVOXATE (IV) (MERCK INDEX, 10th edition 4018)

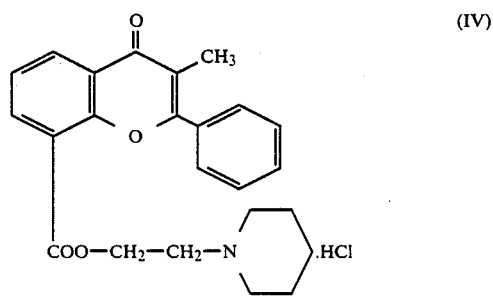

In the compounds represented by the foregoing formula (I), examples of halogen shown by $R_1$, $R_2$, and $R_3$ are fluorine, chlorine, bromine, iodine, examples of lower alkylgroups of straight or branched carbon chain are methyl-, ethyl-, n-propyl-, isopropyl-, n-butyl-, isobutyl-, sec-butyl-, tert-butyl and the like, examples of halogeno-lower alkyl groups are fluoromethyl-, chloromethyl-, difluoromethyl-, trifluoromethyl-, fluoroethyl-and the like, examples of lower-alkoxy groups are methoxy-, ethoxy-, n-propoxy- and the like, and examples of the cycloalkyl group having 3–8 carbon atoms are cyclopropyl-, cyclobutyl-, cycloheptyl-, and cyclooctyl.

Examples of straight or branched lower-alkyl groups represented by $R_4$ are methyl-, ethyl-, n-propyl-, isopropyl-, n-butyl-, isobutyl-, sec-butyl-, tert-butyl-, n-amyl-, isoamyl-, n-hexyl, etc. Examples of pyrrolidinyl-, piperidinyl-, morpholinyl-, and azepinyl groups represented by A are pyrrolidinyl-, 2-methyl-1-pyrrolidinyl-, 1-methyl-2-pyrrolidinyl-, piperidinyl-, 4-methyl-1-piperidinyl-, 4-hydroxy-1-piperidinyl-, 3,5-dimethyl-1-piperidinyl-, 1-ethyl-2-piperidinyl-, 3-methyl-1-piperidinyl-, 4-phenyl-piperidinyl-, morpholinyl-, and azepinyl groups.

The compounds represented by the formula (I) can be converted into the corresponding pharmaceutically-acceptable acid addition salts in a conventional manner and the base can be liberated from the thus-prepared acid addition salts, if necessary.

. Examples of pharmaceutically-acceptable acid addition salts of the compounds represented by formula (I) are salts with mineral acids, such as hydrochloric acid, hydrobromic acid, sulfuric acid, nitric acid, phosphoric acid, and the like, and with an organic acid, such as acetic acid, maleic acid, fumaric acid, citric acid, oxalic acid, lactic acid, tartaric acid, malic acid, and the like.

Representative compounds of the general formula (I) are as follows:
(1) 4'-ethyl-2-methyl-3-pyrrolidinopropiophenone
(2) 4'-cyclohexyl-2-methyl-3-pyrrolidinopropiophenone
(3) 4'-ethyl-2-methyl-3-piperidinopropiophenone
(4) 2, 4'-dimethyl-3-piperidinopropiophenone
(5) 4'-n-butyl-2-methyl-3-pyrrolidinopropiophenone
(6) 2, 4'-dimethyl-3-pyrrolidinopropiophenone
(7) 4'-tert-butyl-2-methyl-3-pyrrolidinopropiophenone
(8) 2-methyl-3',4'-methylenedioxy-3-pyrrolidinopropiophenone
(9) 4'-methoxy-2,2',3'-trimethyl-3-pyrrolidinopropiophenone
(10) 4'-cyclopropyl-2-methyl-3-pyrrolidinopropiophenone
(11) 1-(2,3-dihydro-5-benzofuranyl)-2-methyl-3-pyrrolidino-1-propanone
(12) 5'-chloro-2'-methoxy-3-piperidinopropiophenone
(13) 1-methyl-2-[2-(4-chlorobenzoyl)ethyl] pyrrolidine
(14) 2,2'-dimethyl-3-piperidinopropiophenone
(15) 1-methyl-2-[2-(4-chlorobenzoyl)ethyl] piperidine
(16) 3'-fluoro-2-methyl-3-morpholinopropiophenone
(17) 4'-cyclohexyl-2-methyl-3-pyrrolidinopropiophenone
(18) 4'-fluoromethyl-2-methyl-3-pyrrolidinopropiophenone
(19) 4'-fluoro-2-methyl-3-(1-azepinyl)propiophenone
(20) 3'-fluoro-2-methyl-3-pyrrolidinopropiophenone
(21) 2-methyl-3-pyrrolidinopropiophenone
(22) 4'-ethyl-2-methyl-3-(4-methyl-1-piperidinyl)propiophenone
(23) 4'-ethyl-2-methyl-3-morpholinopropiophenone
(24) 4'-cyclohexyl-3-(4-hydroxy-1-piperidinyl)-2-methyl-propiophenone
(25) 4'-fluoromethyl-2-methyl-3-(4-methyl-1-piperidinyl)propiophenone
(26) 4'-chloro-2-methyl-3-(4-methyl-1-piperidinyl)-propiophenone
(27) 2-methyl-3-(4-methyl-1-piperidinyl)-4'-n-propoxypropiophenone
(28) 3'-methoxy-2-methyl-3-pyrrolidinopropiophenone
(29) 2-methyl-3-(4-methyl-1-piperidinyl)-3',4'-methylenedioxypropiophenone
(30) 1-(2,3-dihydro-5-benzofuranyl)-2-methyl-3-morpholinopropiophenone
(31) 3',4',5'-trimethoxy-2-methyl-3-pyrrolidinopropiophenone
(32) 2,2',4',6'-tetramethyl-3-pyrrolidinopropiophenone
(33) 2',4'-dimethoxy-2,5'-dimethyl-3-morpholinopropiophenone A compound of the present invention represented by genera formula (I) can be administered per os, e.g., in the form of pills or tablets, in which it may be present together with the usual phrmaceutical carriers, conventionally by compounding a compound of this invention together with a customary carrier or adjuvant, such as talc, magnesium stearate, starch, lactose, gelatin, any of numerous gums, and the like. Thus, in their most advantageous form, the compositions of this invention will contain a non-toxic pharmaceutical carrier in addition to the active ingredient of the present invention. Exemplary solid carriers are lactose, magnesium stearate, calcium stearate, starch, terra alba, dicalcium acacia, or the like. Representative liquid carriers are peanut oil, sesame oil, olive oil, water, or the like. The active agents of this invention can be conveniently administered in such compositions containing active ingredient so as to eventually be within the dosage range illustrated hereafter. Thus, a wide variety of pharmaceutical forms suitable for many modes of administration and dosages may be employed. For oral administration, the active ingredient and pharmaceutical forms suitable for many modes of administration and dosages may be employed. For oral administration, the active ingredient and pharmaceutical carrier may, for example, take the form of a granule, pill, tablet, lozenge, elixir, syrup, or other liquid suspension or emulsion whereas, for parenteral administration, the composition may be in the form of a sterile solution.

The method of using the compounds of this invention comprises internally or externally administering a compound of this invention, preferably orally or parenterally and preferably admixed with a pharmaceutical carrier, for example, in the form of any of the above compositions, or filled into a capsule, to alleviate conditions to be treated and symptoms thereof in a living animal body.

The compound of this invention represented by the formula (I) and the acid addition salts thereof can be used by itself, however, they are preferably used together with the pharmacologically- or pharmaceutically-acceptable carrier or adjuvant.

The preparation containing the compound of this invention can be administered preferably per os, by injection, or externally, e.g., in the form of a tablet, capsule, pill, powder, granule, suppository, sterile solution, suspension or emulsion, paste, spray, or the like, in which it may be present together with a carrier or extending agent (lactose, glucose, starch, cristalline cellulose), disintegrating agent (carboxymethylcellulose calcium or the like), binding agent (arginin, gelatin, hydroxypropylcellulose, hydroxypropylmethylcellulose, polyvinylpyrrolidone, or the like), lubricant (magnesium stearate, talc, or the like), coating agent (hydroxypropylmethylcellulose, white sugar, or the like), base (polyethylenglycol, Witepsol and the like).

Illustratively, it may be used in an amount of about 3 to about 500 mg. per unit dose, preferably 15–100 mg for an oral dose, whereas parenteral dosages are usually less and ordinarily about one-half of the oral dose. The unit dose is preferably given a suitable number of times daily, typically three times. The daily dose may vary depending upon the number of times given. Naturally, a suitable clinical dose must be adjusted in accordance with the condition, age, and weight of the patient, and it goes without saying that the enhanced activity of the compounds of this invention, together with their reduced side effects, also makes them suitable for wide variations, and the invention therefore should not be limited by the exact ranges stated. The exact dosage, both unit dosage and daily dosage, will of course have to be determined according to established medical principles.

The effective activity for inhibition of frequency urination- reflex of the propiophenone derivatives represented by formula (I) and the pharmaceutically-acceptable acid addition salts thereof has been determined by tests using animals, wherein the following compounds have been used for the test.

TEST COMPOUND

Compound 1: 4'-ethyl-2-methyl-3-pyrrolidinopropiophenone hydrochloride

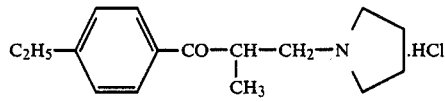

Compound 2: 4'-cyclohexyl-2-methyl-3-pyrrolidinopropiophenone hydrochloride

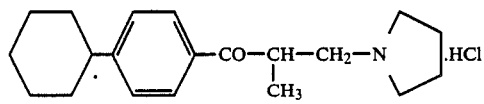

Compound 3: 4'-ethyl-2-methyl-3-piperidinopropiophenone hydrochloride
(II), (Eperisone Hydrochloride)

Compound 4: 2,4'-ethyl-2-methyl-3-piperidinopropiophenone hydrochloride
(III), (Tolperisone Hydrochloride)

Compound 5: 4'-methoxy-2,2',3'-trimethyl-3-pyrrolidinopropiophenone hydrochloride

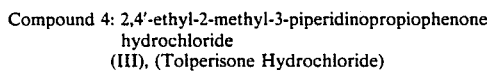
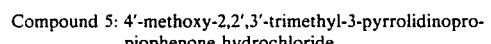

Compound 6: 1-methyl-2-[2-(4-chlorobenzoyl)ethyl]pyrrolidine hydrochloride

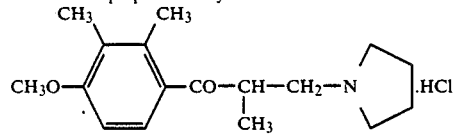

Compound 7: 3'-fluoro-2-methyl-3-morpholinopropiophenone hydrochloride

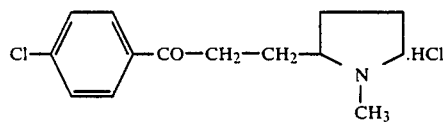

Compound 8: 4'-fluoromethyl-2-methyl-3-pyrrolidinopropiophenone hydrochloride

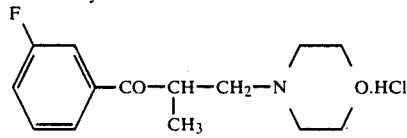

Compound 9: 4'-fluoro-2-methyl-3-(1-azepinyl)propiophenone hydrochloride

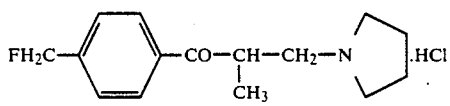

Reference Compound: FLAVOXATE(IV)

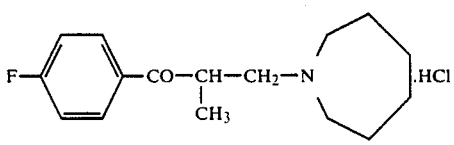

EFFECT

The propiopheneone derivatives of this invention above shown in general structure (I) and their pharmacologically-acceptable acid addition salts were shown to possess a potent micturition reflex inhibition effect, for example, an inhibitory effect on the rhythmic bladder contractions and delayed effects on the cystometrograms, in the following animal experiments.

1. Inhibition effect on the rhythmic bladder contractions of rats in anesthetized and intravenous administration.
2. Inhibition effect on the rhythmic bladder contractions of rats in unanesthetized (immobilized with gallamine) or intraduodenal administration.
3. Delayed effect on the cystometrograms induced by saline infusion in dogs, cats and rats.
4. Micturition inhibition effect in hypogastric nerve (concerned with micturition reflex inhibition) in transected rats which were considered a neurogenic pollakiuria model.

In comparison with flavoxate hydrochloride, used as an anti-pollakiura agent at present, these effects of the compounds of this invention were equal or more potent in anesthetized and in intravenous administration, and more potent in unanesthetized or in intraduodeunum administration.

statistical analysis: Each data of Experiment 1-6 represents the mean±S.E. statistical analysis of the data was performed using student's t-test.

EXPERIMENTS

EXAMPLE 1

Inhibition effects on the micturition reflex (rhythmic bladder contractions, in anesthetized rats)

According to the method described by Morikawa et al. (Folia phamacol. japon.: 88,355 (1986), male wister rats weighing about 300 g (in case of intraduodenal administration, fasted 18-20 hours) were anesthetized with urethane (500 mg/kg, i.p.) and alpha-chloralose (50 mg/kg, i.p.), and fixed on their back.

Then, through a midline incision of the abdomen, the urinary bladder was exposed, provided with a small incision, and a balloon (capacity about 1 ml) was inserted into the bladder dome.

The balloon was connected to a pressure transducer and variations of inside pressure were recorded on a recorder.

Micturition reflex was elicited by elevating balloon pressure 10-20 cm $H_2O$.

In case of intravenous administration, the drug was administrated through a cannula inserted into the left jugular vein and, in case of intraduodenum administration, the drug was administrated through a cannula into the duodenum from outside the stomach.

In case of intravenous administration, the drug was evaluated by the dissappearance time of bladder contractions caused by micturition reflex.

These results are shown in Table 1.

In case of intraduodenal administration, the sum total of amplitude of bladder contractions caused by the micturition reflex was calculated during each five minutes at 5 min. before and 15, 30, 45, and 60 min. after the administration.

Then, the maximum inhibition rate was determined from one of the above judgment times compared with that of before the administration, and the dose which inhibited 50 percent of the sum total of amplitude of bladder contractions during five minutes ($ED_{50}$ value), was calculated from the graph.

These results are shown in Table 2.

TABLE 1

(In intravenous administration)

| Test Drug | Dose (mg/kg, i.v.) | No. of Rats | Disappearance time (min ± S.E.) | $ED_3$# (mg/kg, i.v.) |
|---|---|---|---|---|
| Compound 1 | 1 | 3 | 1.1 ± 1.1 | 2.2 |
|  | 2 | 3 | 2.3 ± 0.5 |  |
|  | 4 | 3 | 7.1 ± 2.8 |  |
| Compound 2 | 1 | 3 | 1.0 ± 1.0 | 2.2 |
|  | 2 | 3 | 2.5 ± 1.3 |  |
|  | 4 | 3 | 6.3 ± 0.8 |  |
| Compound 3 | 1 | 3 | 0.4 ± 0.4 | 1.4 |
|  | 2 | 3 | 5.3 ± 2.6 |  |
|  | 4 | 3 | 12.0 ± 1.2 |  |
| Compound 4 | 1 | 3 | 1.0 ± 0.7 | 2.4 |
|  | 2 | 3 | 2.3 ± 0.5 |  |
|  | 4 | 3 | 4.9 ± 1.9 |  |
| Compound 5 | 0.25 | 3 | 3.0 ± 0.4 | 0.25 |
|  | 1 | 3 | 6.3 ± 1.4 |  |
| Compound 6 | 2 | 3 | 1.1 ± 0.3 | 8.0 |
|  | 4 | 3 | 1.9 ± 0.3 |  |
|  | 8 | 3 | 3.0 ± 0.3 |  |
| Compound 7 | 2 | 3 | 1.8 ± 1.0 | 2.8 |
|  | 8 | 3 | 6.8 ± 2.1 |  |
| Compound 8 | 2 | 3 | 1.5 ± 0.9 | 4.7 |
|  | 4 | 3 | 2.4 ± 2.0 |  |
|  | 8 | 3 | 5.2 ± 2.5 |  |
| Compound 9 | 1 | 3 | 0.5 ± 0.1 | 2.7 |
|  | 2 | 3 | 1.2 ± 0.8 |  |
|  | 4 | 3 | 5.5 ± 2.7 |  |
| Compared drug | 1 | 3 | 1.1 ± 1.1 | 1.4 |
| flavoxate-HCl | 3 | 3 | 7.5 ± 2.7 |  |

: The dose at which rhythmic bladder contractions disappeared in three (3) minutes

TABLE 2

(In intraduodenal administration)

| Test Drug | $ED_{50}$ (mg/kg) |
|---|---|
| Compound 1 | 14.3 |
| Reference Compound | 270.0 |

All the compounds of this invention showed potent micturition reflex inhibition.

In further comparisons, the compounds of this invention showed a micturition reflex inhibition effect almost equally potent to the reference drug in intravenous administration, and more potent in intraduodenal administration.

Example 2

Inhibition effects on the micturition reflex (rhythmic bladder contractions, in anesthetized rats)

Male Wister rats weighing about 300 g (in case of intraduodenal administration, fasted more than 15 hours) were anesthetized with ether and immobilized with gallamine (5 mg/kg, i.v.) and fixed on their back. As soon as that procedure was finished anesthesia was discontinuted.

In the experiment, infusion of gallamine, 13 mg/kg/hr, i.v. (in case of intraduodenum administration, 10 mg/kg/hr, i.v.) was continuted, and artificial respiration was performed (90 times/min, 3 ml air/time).

Then, through a midline incision of the abdomen, the urinary bladder was exposed; a small incision provided therein, and a balloon (capacity about 1 ml) was inserted into the bladder dome.

The balloon was connected to a pressure transducer and variations of inside pressure were recorded on a recorder.

Micturition reflex was elicited by raising the balloon pressure 10–20 cm $H_2O$.

In case of intravenous administration, the drug was administrated through a cannula inserted into the left jugular vein, and in case of intraduodenal administration the drug was administrated through a cannula inserted into the duodenum from outside the stomach.

In case of intravenous administration, the effect of the drug was represented by the disappearance time of bladder contractions caused by micturition reflex.

These results are shown in Table 3.

In case of intraduodenal administration, the sum total of amplitude of bladder contractions caused by micturition reflex was calculated during each five minutes at 5 min before and 15, 30, 45, 60, 75, 90, 105 and 120 min after the administration.

Then, inhibition rate was calculated by the sum total of amplitude of bladder contractions at each point compared with that before the administration.

The peak of effect was at 15 min after the administration in each dose.

These results are shown in Table 4.

TABLE 3

(In intravenous administration)

| Test Drug | Dose (mg/kg, i.v.) | No. of Rats | Disappearance time (min ± S.E.) |
|---|---|---|---|
| Saline | — | 4 | 9.0 ± 1.8 |
| Compound 1 | 4 | 4 | 52.8 ± 23.4 |
|  | 8 | 4 | 249.0 ± 45.0* |

*Significant different from control at $p < 0.05$

TABLE 4

(In intraduodenal administration)

| Test Drug | Dose (mg/kg, i.d) | No. of Rats | Inhibition Rate (%) |
|---|---|---|---|
| 0.5% CMC | — | 5 | 11.9 ± 7.9 |
| Compound 1 | 12.5 | 4 | 36.1 ± 4.4* |
|  | 25 | 4 | 53.8 ± 6.9** |
|  | 50 | 4 | 87.9 ± 5.1** |

*, **Significant different from control at $p < 0.05$, $p < 0.01$ (15 min after administration)

In case of intravenous administration, the compound of this invention had a potent inhibitory effect on the micturition reflex, and the effect of 8 mg/kg, i.v. was significant in comparison with the control.

In case of intraduodenal administration, the compound of this invention shows significant effect in comparison with the control, and that effect was dose dependent.

These results show that the compounds of this invention also have an inhibitory effect on the micturition reflex in unanesthetized condition.

EXAMPLE 3

Effects on the cystometrogram (Dog)

Mongrel adult dogs weighing about 10 kg were anesthetized with thiopental (20 mg/kg, i.v.) and immobilized with gallamine (2 mg/kg, i.v.), and fixed on their back.

In the experiment, infusion of pentobarbital (3 mg/kg/hr, i.v.) and gallamine (3 mg/kg i.v.) were continuted, and artifical respiration was performed (20 times/min, 20 ml air/kg).

After midline incision of the abdomen, the ureters were ligated and polyethylene tubes were inserted into the kidney side and the urinary bladder side. Urine was led out of the body from the kidney side, and warm saline was infused using a continuous infusion pump from the urinary bladder side.

Then, a catheter was inserted into the bladder dome and connected to a pressure transducer. Intravesical pressure was recorded on a recorder.

The infusion rate of saline was changed (6-35 ml/min) so as to induce the time to micturition from the saline infusion (time to micturition) at about five minutes.

The drug was administered (through a cannula inserted into the right femoral vein) at the second minute before the last time to micturition, and the delayed time of micturition was evaluated.

These results are shown in Table 5.

TABLE 5

| | (In intravenous administration) | | |
|---|---|---|---|
| Test Drug | Dose (mg/kg, i.v.) | No of Dogs | Delayed time of Micturition (second ± S.E.) |
| Saline | — | 5 | 6.0 ± 13.8 |
| Compound 1 | 1 | 5 | 13.2 ± 21.0 |
| | 3 | 4 | 50.4 ± 15.0* |
| Reference Drug | 1 | 7 | 0.6 ± 35.4 |
| | 3 | 5 | 30.6 ± 44.4 |

*Significant different from last time to micturition at $p < 0.05$

In dogs, the compound of this invention also had a more potent effect in delaying time of micturition than the reference drug.

EXAMPLE 4

Effects on the cystometrogram (Cat)

Mongrel adult cats weighing about 3 kg (in case of intraduodenal administration, fasted 24 hours) were anesthetized with urethane (500 mg/kg, i.p.) and alpha-chloralose (50 mg/kg, i.p.) and fixed on their back.

After midline incision of the abdomen, the ureters were ligated and polyethylene tubes were inserted into the kidney side and urinary bladder side, urine was led out of the body from the kidney side, and warm saline was infused using a continuous infusion pump from the urinary bladder side.

Then, a catheter was inserted into the bladder dome and connected to a pressure transducer Intravesical pressure was recorded on a recorder.

The infusion rate of saline was changed (0.7-6.6 ml/min) so as to induce the time to micturition from saline infusion at about five minutes.

Each of delayed time of micturition was evaluated. In case of intravenous administration, the drug was administered through a cannula inserted into the right femoral vein at 30 seconds before saline infusion.

These results are shown in Table 6.

In case of intraduodenal administration, the drug was administrated through a tube inserted into the duodenum by way of mouth at the time of saline infusion, and the time to micturition was measured at 15 min. intervals until 90 min.

These results at 30 min. after administration are shown in Table 7.

TABLE 6

| | In intravenous administration | | | |
|---|---|---|---|---|
| Test drug | Dose (mg/kg; i.v.) | No. of Cats | Delayed time to micturition (second ± S.E.) | ED₂# (mg/kg;i.v.) |
| Saline | — | 6 | 6.6 ± 10.2 | — |
| Compound 1 | 1 | 5 | −19.2 ± 6.6 | |
| | 4 | 5 | 70.8 ± 27.0 | 5.6 |
| | 8 | 5 | 170.4 ± 48.0 | |
| Reference drug | 1 | 5 | 12.0 ± 10.8 | — |
| | 4 | 7 | 39.0 ± 43.8 | |
| | 8 | 4 | −16.8 ± 36.6 | |

: The dose which delayed time to micturition by 2 min.
*: Significant difference from control at $p < 0.05$

TABLE 7

| | In intraduodenal administration (after 30 min.) | | | |
|---|---|---|---|---|
| Test drug | Dose (mg/kg; i.d.) | No. of Cats | Delayed time to micturition (second ± S.E.) | ED₂# (mg/kg;i.d.) |
| Water | — | 5 | 22.2 ± 16.2 | — |
| Compound 1 | 12.5 | 3 | 49.8 ± 8.4 | |
| | 25.0 | 4 | 105.0 ± 10.8** | 39 |
| | 50.0 | 4 | 128.4 ± 37.8 | |
| Reference drug | 30.0 | 4 | −45.6 ± 37.8 | |

: The dose which delayed time to micturition by 2 min.
**: Significant different from control at $p < 0.01$ The compound of this invention showed potent delayed effect on the cystometogram in intravenous and intraduodenal administration in cats.

On the other hand, the reference drug was not recognized to produce delayed effects in the cat.

EXAMPLE 5

Effects on the cystometrogram (in anesthetized rat)

Male Wister rats weighing about 300 g were anesthetized with urethane (500 mg/kg, i.p.) and α-chloralose (50 mg/kg, i.p.) and fixed on their back.

Then, through a midline incision of the abdomen, the urinary bladder was exposed, provided with a small incision, a polyethylene tube was inserted into the bladder dome, and ureters were cut.

Then, through the polyethylene tube, saline was infused using a continuous infusion pump. On the other hand, the polyethylene tube was connected to a pressure transducer. Intravesical pressure was recorded on a recorder.

The drug was administrated through a cannula inserted into the left jugular vein at 30 sec before saline infusion. Effect of the drug was represented by delayed time to micturition.

These results are shown in Table 8.

TABLE 8

| | In intraduodenal administration | | |
|---|---|---|---|
| Test drug | Dose (mg/kg; i.v.) | No. of Rats | Delayed time of micturition (second ± S.E.) |
| Saline | — | 6 | −6.0 ± 49.8 |
| Compound 1 | 1 | 6 | 52.8 ± 50.4 |
| | 4 | 6 | 102.0 ± 32.4 |
| | 8 | 6 | 200.4 ± 60.6** |

**: Significant different from control at $P < 0.01$

The compound of this invention had a delayed effect from 1 mg/kg i.v. and that effect was dose dependent.

The effect of 8 mg/kg i.v. was significant in comparson with control.

These results confirmed that the compound of this invention had an inhibitory effect on the micturition reflex in rats, both in the method of rhythmic bladder contractions (Examples 1 and 2), and in the method of cystometrograms (Example 5)

EXAMPLE 6

Effect on the cystometrogram (pollakiuria model rats induced by hypogastric nerve transection)

Male Wister rats weighing 300 g were incised midline of the abdomen, and bilateral hypogastric nerves were transected.

Two days after hypogastric nerve transection, the rats were anesthetized with urethane (500 mg/kg, i.p.) and alpha-chloralose (50 mg/kg, i.p.) and fixed on their back.

Then, through a midline incision of the abdomen, the urinary bladder was exposed, provided with a small incision, a polyethylene tube inserted, and ureters were cut.

Through the polyethylene tube, saline was infused using a continuous infusion pump. On the other hand, the polyethylene tube was connected to a pressure transducer. Intravesical pressure was recorded on a recorder.

The drug was administered through a cannula inserted into the left jugular vein at 30 sec before saline infusion.

Effect of drug was represented as delayed time to micturition.

These results are shown in Table 9.

TABLE 9

| | (In Intravenous administration) | | |
|---|---|---|---|
| Test drug | Dose (mg/kg; i.v.) | No. of Rats | Delayed time of micturition (second ± S.E.) |
| Saline | — | 5 | −6.0 ± 31.8 |
| Compound 1 | 1 | 5 | 91.8 ± 47.4 |
| | 4 | 5 | 179.4 ± 111.0 |
| | 8 | 6 | 449.4 ± 65.4** |

**: Significant different from control at P < 0.01

This invented compound had a delayed effect from 1 mg/kg; i.v. and that effect was dose dependent, and that effect of 8 mg/kg; i.v. was significant in comparison with control.

These results represented that even if in a neurogenic pollakiuria model rats induced by hypogastric nerve transected, this invented compound had also inhibition effect on the micturition reflex.

EXAMPLE 7

Five to ten male ddY mice aged 4–5 weeks were used for each determination.

The test drug (5–8 dose levels) was orally administrated, and the LD50 value was calculated by Probit method from the mortality for one week after administration.

These results are shown in Table 10.

TABLE 10

| (In oral administration) | |
|---|---|
| Test drug | LD 50 (mg/kg. p.o.) |
| Compound 1 | 425 |
| Compound 2 | 587 |
| Compound 3 | 332 |
| Compound 4 | 450 |
| Reference drug | 1,333 |

We claim:

1. A method for the treatment of pollakiurea in a subject in need thereof, comprising the step of administering to said subject an effective antipollakiurea amount of a propiophenone of the Formula (I)

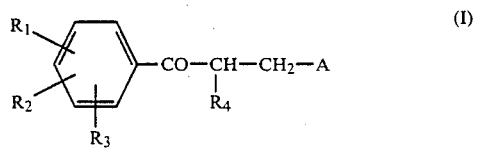

wherein $R_1$, $R_2$ and $R_3$ each independently represents hydrogen, halogen, lower alkyl- or halogeno-lower-alkyl, lower-alkoxy, or cycloalkyl having 3–8 carbon atoms, two of which $R_1$, $R_2$, and $R_3$ groups may combine to form methylenedioxy or ethyleneoxy, $R_4$ represents hydrogen or lower-alkyl, and A represents pyrrolidinyl-, piperidinyl-, or a pharmaceutically-acceptable acid addition salt thereof.

2. Method of claim 1, wherein the propiophenone is selected from the group consisting of
    4'-ethyl-2-methyl-3-pyrrolidinopropiophenone,
    4'cyclohexyl-2-methyl-3-pyrrolidinopropiophenone,
    4'-ethyl-2-methyl-3-piperidonopropiophenone, and
    2,4'-dimethyl-3-piperidinopropiophenone, and pharmaceutically-acceptable salts thereof.

3. Method of claim 1, wherein the propiophenone is administered in an amount of about 3 to about 500 mg. per unit dose.

4. Method of claim 1, wherein the propiophenone is administered orally in an amount of about 15 to 100 mg. per oral dose.

5. Method of claim 1, wherein the propiophenone is administered in the form of a pharmaceutical composition thereof together with a pharmaceutically-acceptable diluent or carrier.

6. Method of claim 5, wherein the pharmaceutical composition is suitable for oral administration and is administered orally.

7. Method of claim 1 wherein the propiophenone is selected from the group consisting of
    4'-n-butyl-2-methyl-3-pyrrolidinopropiophenone,
    4'-tert-butyl-2-methyl-3-pyrrolidinopropiophenone, and
    4'-methoxy-2,2',3'-trimethyl-3-pyrrolidinopropiophenone, and pharmaceutically-acceptable salts thereof.

* * * * *

UNITED STATES PATENT AND TRADEMARK OFFICE
CERTIFICATE OF CORRECTION

PATENT NO. : 4,912,116

DATED : Mar. 27, 1990

INVENTOR(S) : Yasuo Itoh, Hideo Kato, Eiichi Koshinaka, Kouji Morikawa, Toshie Yamauchi It is certified that error appears in the above-identified patent and that said Letters Patent is hereby corrected as shown below:

Column 1, line 27/28 "pyrrolindinyl-," should read
-- pyrrolidinyl-, --.
Column 1, line 48; "9351," should read -- 9353, --.
Column 3, line 60; "genera" should read -- general --.
Column 8, line 35; "different" should read -- difference --.
Column 8, approximately line 45; "different" should read
-- difference --.
Column 8/9, last line of 8, first line of 9; "continuted,"
-- continued, --.
Column 9, approximately line 32; "different" should read
-- difference --.
Column 9, line 52; "transducer Intravesical" should read
-- transducer. Intravesical --.
Column 10, approximately line 28; "different" should read
-- difference --.
Column 10,line 65; "different" should read -- difference --.
Column 11, line 1; "comparson" should read -- comparison --.
Column 11, line 45; "different" should read -- difference --.
Column 9, line 63; "administrated" should read --administered--.

Signed and Sealed this

Fifth Day of November, 1991

Attest:

HARRY F. MANBECK, JR.

Attesting Officer

Commissioner of Patents and Trademarks